(12) United States Patent
Fukuzawa

(10) Patent No.: US 11,607,687 B2
(45) Date of Patent: Mar. 21, 2023

(54) REACTION TREATMENT CONTAINER AND REACTION TREATMENT DEVICE

(71) Applicant: Nippon Sheet Glass Company, Limited, Tokyo (JP)

(72) Inventor: Takashi Fukuzawa, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 358 days.

(21) Appl. No.: 16/398,440

(22) Filed: Apr. 30, 2019

(65) Prior Publication Data

US 2019/0255525 A1    Aug. 22, 2019

Related U.S. Application Data

(63) Continuation of application No. PCT/JP2017/038252, filed on Oct. 24, 2017.

(30) Foreign Application Priority Data

Nov. 1, 2016   (JP) .............................. JP2016-214059

(51) Int. Cl.
*B01L 3/00* (2006.01)
*B01L 7/00* (2006.01)
(Continued)

(52) U.S. Cl.
CPC ..... *B01L 3/502746* (2013.01); *B01J 19/0093* (2013.01); *B01L 3/502715* (2013.01);
(Continued)

(58) Field of Classification Search
CPC ..... B01L 2400/0487; B01L 2300/0883; B01L 3/502723
(Continued)

(56) References Cited

U.S. PATENT DOCUMENTS

| 5,304,487 A | 4/1994 | Wilding et al. |
| 9,403,165 B2 | 8/2016 | Williams et al. |

(Continued)

FOREIGN PATENT DOCUMENTS

| CN | 202018437 U | 10/2011 |
| CN | 102653715 A | 9/2012 |

(Continued)

OTHER PUBLICATIONS

Invitation to Respond to Written Opinion dated Feb. 3, 2020, from the Intellectual Property Office of Singapore in Application No. 11201903603S.
(Continued)

*Primary Examiner* — Natalia Levkovich
(74) *Attorney, Agent, or Firm* — Sughrue Mion, PLLC

(57) ABSTRACT

A reaction processing vessel includes: a substrate; a channel for a sample to move that is formed on the substrate; a first air communication port and a second air communication port provided at respective ends of the channel; and a thermal cycle region for applying a thermal cycle to the sample that is formed between the first air communication port and the second air communication port in the channel. The channel includes a first branch channel and a second branch channel between the thermal cycle region and the first air communication port.

9 Claims, 6 Drawing Sheets

(51) Int. Cl.
  *C12M 1/00*    (2006.01)
  *G01N 37/00*   (2006.01)
  *B01J 19/00*   (2006.01)
(52) U.S. Cl.
  CPC ............. *B01L 7/52* (2013.01); *C12M 1/00* (2013.01); *G01N 37/00* (2013.01); *B01J 19/00* (2013.01); *B01L 2200/026* (2013.01); *B01L 2200/0694* (2013.01); *B01L 2400/0487* (2013.01)
(58) Field of Classification Search
  USPC ...................................... 422/82.12, 507, 504
  See application file for complete search history.

(56) References Cited

U.S. PATENT DOCUMENTS

| | | | | |
|---|---|---|---|---|
| 2007/0111299 | A1* | 5/2007 | Woudenberg | B01L 3/502715 435/287.1 |
| 2017/0175067 | A1 | 6/2017 | Tachibana et al. | |

FOREIGN PATENT DOCUMENTS

| | | | |
|---|---|---|---|
| JP | 07506258 | A | 7/1995 |
| JP | 2004305009 | A | 11/2004 |
| JP | 2005253466 | A | 9/2005 |
| JP | 2006094866 | A | 4/2006 |
| JP | 2009189295 | A | 8/2009 |
| JP | 2009232700 | A | 10/2009 |
| JP | 4539125 | B2 | 9/2010 |
| JP | 2011200193 | A | 10/2011 |
| JP | 2011528552 | A | 11/2011 |
| JP | 4993260 | B2 | 8/2012 |
| JP | 2013055921 | A | 3/2013 |
| JP | 2014212705 | A | 11/2014 |
| RU | 2385940 | C1 | 4/2010 |
| WO | 93/22053 | A1 | 11/1993 |
| WO | 2013132645 | A1 | 9/2013 |
| WO | 2015019626 | A1 | 2/2015 |
| WO | 2015078998 | A1 | 6/2015 |
| WO | 2016021158 | A1 | 2/2016 |
| WO | 2017094674 | A1 | 6/2017 |
| WO | 2017119382 | A1 | 7/2017 |
| WO | 2017199933 | A1 | 11/2017 |

OTHER PUBLICATIONS

Communication dated Jul. 7, 2020, from the Russian Federal Service for Intellectual Property in Application No. 2019116867/10.
Communication dated May 25, 2021 by the Intellectual Property Office on Singapore in application No. 11201903603S.
Communication dated May 6, 2020, from the European Patent Office in European Application No. 17866503.0.
Communication dated Mar. 15, 2021 from the Republic of Indonesia Directorate General of Intellectual Property in Application No. PID201904576.
Notification of Reasons for Refusal dated May 28, 2019 from the Japanese Patent Office in application No. 2018-548947.
International Preliminary Report on Patentability and Translation of Written Opinion, dated May 7, 2019 from the International Bureau in counterpart International application No. PCT/JP2017/038252.
International Search Report, dated Jan. 23, 2018 from the International Bureau in counterpart International application No. PCT/JP2017/038252.
Office Action dated May 16, 2022 issued by the Chinese Patent Office in Chinese Application No. 201780065196.4.
Communication dated Jun. 30, 2021 from the Indian Patent Office in Application No. 201917017722.
Office Action dated Oct. 31, 2022 in Vietnamese Application No. 1-2019-02662.
Communication dated Nov. 2, 2021 from the Japanese Patent Office in Japanese Application No. 2019-142779.
Communication dated Nov. 3, 2021 from the Chinese Patent Office in Chinese Application No. 201780065196.4.
Communication dated Nov. 22, 2021 from the Saudi Arabian Patent Office in Saudi Arabian Application No. 519401674.

\* cited by examiner

REACTION TREATMENT CONTAINER AND REACTION TREATMENT DEVICE

BACKGROUND OF THE INVENTION

1. Field of the Invention

The present invention relates to reaction processing vessels and reaction processors used for polymerase chain reactions (PCR).

2. Description of the Related Art

Genetic testing is widely used for examinations in a wide variety of medical fields, identification of farm products and pathogenic microorganisms, safety assessment for food products, and even for examinations for pathogenic viruses and a variety of infectious diseases. In order to detect with high sensitivity a minute amount of gene's DNA, methods of analyzing the resultant obtained by amplifying a portion of DNA are known. Above all, PCR is a remarkable technology where a certain portion of a very small amount of DNA collected from an organism or the like is selectively amplified.

In PCR, a predetermined thermal cycle is applied to a sample in which a biological sample containing DNA and a PCR reagent consisting of primers, enzymes, and the like are mixed so as to cause denaturation, annealing, and elongation reactions to be repeated so that a specific portion of DNA is selectively amplified.

It is a common practice to perform PCR by putting a predetermined amount of a target sample into a PCR tube or a reaction processing vessel such as a microplate (microwell) in which a plurality of holes are formed. However, in recent years, PCR using a reaction processing vessel (also referred to as "chip") provided with a micro-channel that is formed on a substrate is practiced (e.g. Patent Document 1).

[Patent Document 1] JP 2009-232700

SUMMARY OF THE INVENTION

In PCR, for example, it is necessary to repeat a thermal cycle on a sample for a predetermined number of times by moving the sample such that the sample reciprocates between a region of a channel in which the temperature is maintained at a medium temperature of around 60° C. and a region of a channel in which the temperature is maintained at a high temperature of around 95° C. Since the sample is normally an aqueous solution, the vapor pressure becomes high in a high temperature region of around 95° C., and the water content of the sample is likely to evaporate. A portion of the water content of the sample that has evaporated condenses or forms dew at a part of the channel where the temperature is relatively low forming a mass of liquid, which can block the channel. When the channel is blocked by a mass of liquid in this way, there is a possibility that the thrust does not suitably act on the sample even when the inside of the channel is pressurized such that the sample cannot be appropriately moved. If the sample cannot be moved appropriately as described, a stable PCR may not be able to be performed.

In this background, a purpose of the present invention is to provide a reaction processing vessel and a reaction processor that allow a stable PCR to be performed by appropriately moving a sample.

A reaction processing vessel according to one embodiment of the present invention includes: a substrate; a channel for a sample to move that is formed on the substrate; a pair of air communication ports provided at respective ends of the channel; and a thermal cycle region for applying a thermal cycle to the sample that is formed between the pair of air communication ports in the channel. The channel includes a plurality of branch channels between the thermal cycle region and at least one of the air communication ports.

The thermal cycle region may include a first temperature region maintained at a first temperature and a second temperature region maintained at a second temperature that is higher than the first temperature. The plurality of branch channels may be arranged between the second temperature region and an air communication port located on the side of the second temperature region.

A branching part of the channel in the thermal cycle region and the plurality of branch channels may be arranged near the second temperature region.

At least one of the plurality of branch channels may be arranged so as to pass near the second temperature region.

The plurality of branch channels may each include a bent part. The bent part of at least one of the plurality of branch channels may be bent with a curvature radius that is larger than that of the bent parts of other branch channels.

Another embodiment of the present invention relates to a reaction processor. This reaction processor includes: a reaction processing vessel described above; a temperature control unit for adjusting the temperature of the thermal cycle region; and a liquid feeding system that moves and stops a sample in the channel.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1A:
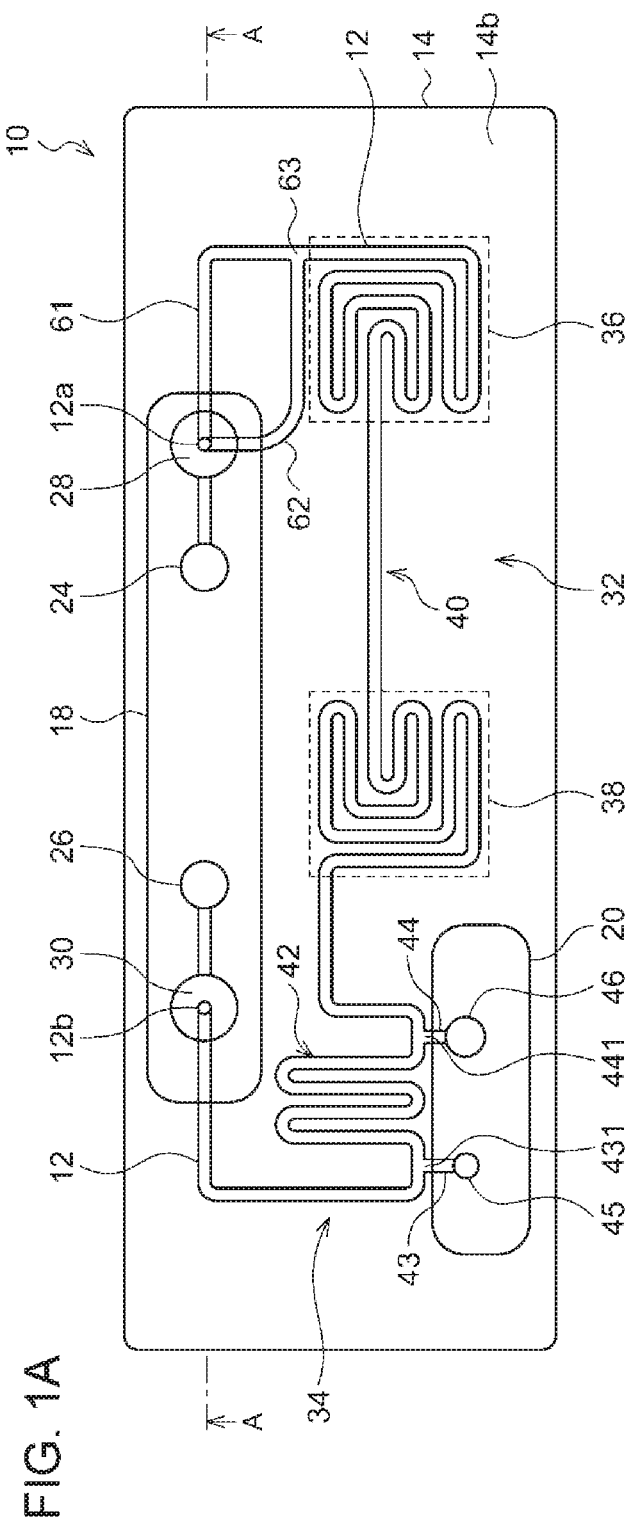
FIGS. 1A and 1B are diagrams for explaining a reaction processing vessel according to an embodiment of the present invention.

An explanation will be given in the following regarding a reaction processing vessel and a reaction processor according to an embodiment of the present invention. The same or equivalent constituting elements, members, and processes illustrated in each drawing shall be denoted by the same reference numerals, and duplicative explanations will be omitted appropriately. Further, the embodiments do not limit the invention and are shown for illustrative purposes, and all the features described in the embodiments and combinations thereof are not necessarily essential to the invention.

Figure 1B:
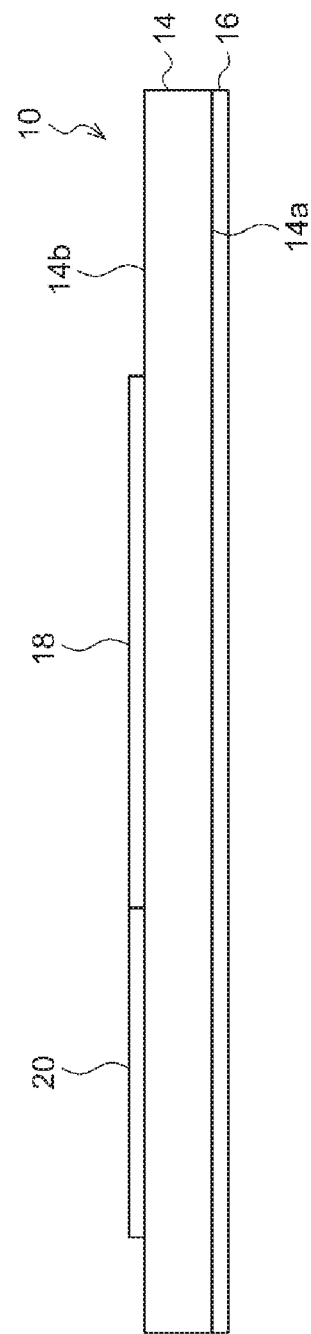
Figure 2:
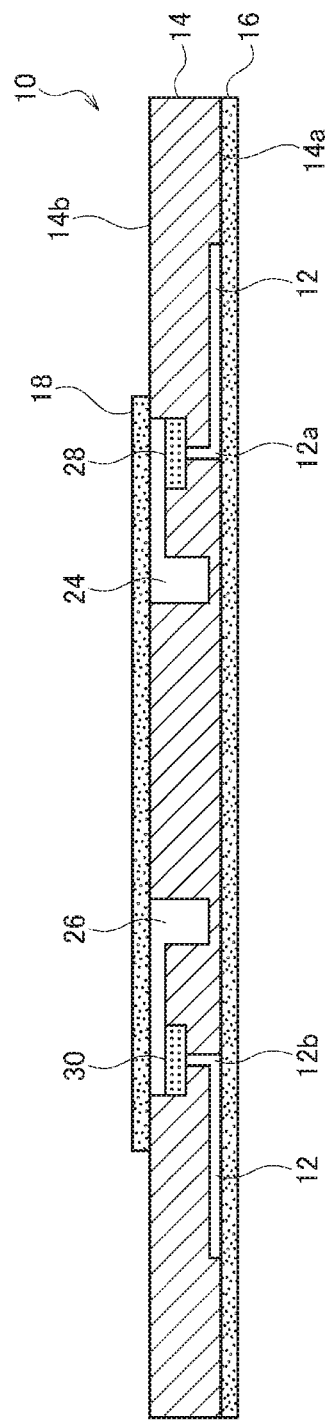
FIG. 2 is a cross-sectional view of the reaction processing vessel shown in FIG. 1A that is sectioned along line A-A.
Figure 3:
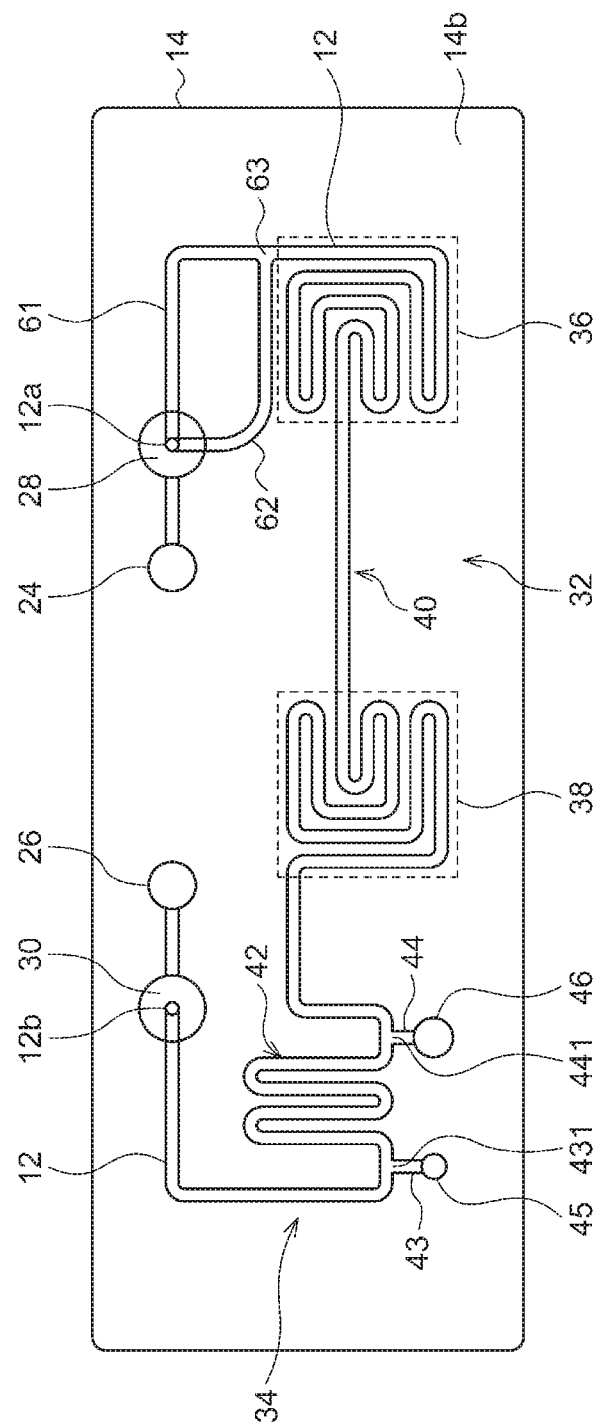
FIG. 3 is a plan view of a substrate provided in the reaction processing vessel.

FIGS. 1A and 1B are diagrams for explaining a reaction processing vessel 10 according to an embodiment of the present invention. FIG. 1A is a plan view of the reaction processing vessel 10, and FIG. 1B is a front view of the reaction processing vessel 10. FIG. 2 is a cross-sectional view of the reaction processing vessel 10 shown in FIG. 1A that is sectioned along line A-A. FIG. 3 is a plan view of a substrate 14 provided in the reaction processing vessel 10.

The reaction processing vessel 10 comprises a resinous substrate 14 having a groove-like channel 12 formed on a lower surface 14a thereof, a channel sealing film 16, which is attached on the lower surface 14a of the substrate 14, for sealing the channel 12, and two sealing films (a first sealing film 18 and a second sealing film 20) attached on an upper surface 14b of the substrate 14.

The substrate 14 is preferably formed of a material that is stable under temperature changes and is resistant to a sample solution that is used. Further, the substrate 14 is preferably formed of a material that has good moldability, a good transparency and barrier property, and a low self-fluorescent property. As such a material, an inorganic material such as glass, silicon (Si), or the like, a resin such as acrylic, polyester, silicone, or the like, and particularly a cycloolefin polymer resin (COP) are preferred. An example of the dimensions of the substrate 14 includes a long side of 76 mm, a short side of 26 mm, and a thickness of 4 mm.

The groove-like channel 12 is formed on the lower surface 14a of the substrate 14. In the reaction processing vessel 10 according to the present embodiment, most of the channel 12 is formed in the shape of a groove exposed on the lower surface 14a of the substrate 14. This is for the purpose of allowing for easy molding through injection molding using a metal mold or the like. In order to seal this groove so as to make use of the groove as a channel, the channel sealing film 16 is attached on the lower surface 14a of the substrate 14. An example of the dimensions of the channel 12 includes a width of 0.7 mm and a depth of 0.7 mm.

The channel sealing film 16 may be sticky on one of the main surfaces thereof or may have a functional layer that exhibits stickiness or adhesiveness through pressing, energy irradiation with ultraviolet rays or the like, heating, etc., formed on one of the main surfaces. Thus, the channel sealing film 16 has a function of being easily able to become integral with the lower surface 14a of the substrate 14 while being in close contact with the lower surface 14a. The channel sealing film 16 is desirably formed of a material, including an adhesive, that has a low self-fluorescent property. In this respect, a transparent film made of a resin such as a cycloolefin polymer, polyester, polypropylene, polyethylene or acrylic is suitable but is not limited thereto. Further, the channel sealing film 16 may be formed of a plate-like glass or resin. Since rigidity can be expected in this case, the channel sealing film 16 is useful for preventing warpage and deformation of the reaction processing vessel 10.

A first air communication port 24 is formed at the position of one end 12a of the channel 12 in the substrate 14. A second air communication port 26 is formed at the position of the other end 12b of the channel 12 in the substrate 14. The pair, the first air communication port 24 and the second air communication port 26, is formed so as to be exposed on the upper surface 14b of the substrate 14.

A first filter 28 is provided between the first air communication port 24 and one end 12a of the channel 12 in the substrate 14. A second filter 30 is provided between the second air communication port 26 and the other end 12b of the channel 12 in the substrate 14. The pair, the first filter 28 and the second filter 30, provided at respective ends of the channel 12, has good low impurity characteristics and also allows only air to pass therethrough so as to prevent contamination so that the amplification of target DNA and the detection of the amplification are not interrupted by PCR or so that the quality of the target DNA does not deteriorate. As a filter material, for example, a material obtained by subjecting polyethylene to a water repellent treatment can be used. Alternatively, a known material can be selected as long as the material has the above function. Regarding the dimensions of the first filter 28 and the second filter 30, the first filter 28 and the second filter 30 are formed so as to fit without any gap in a filter installation space formed in the substrate 14 and may have, for example, a diameter of 4 mm and a thickness of 2 mm.

As shown in FIG. 1A, between the pair consisting of the first air communication port 24 and the second air communication port 26, the channel 12 includes a thermal cycle region 32 for applying a thermal cycle to the sample and a dispensing region 34 for performing so-called dispensing where a predetermined amount of the sample is extracted. The thermal cycle region 32 is located on the side of the first air communication port 24 in the channel 12. The dispensing region 34 is located on the side of the second air communication port 26 in the channel 12. The thermal cycle region 32 and the dispensing region 34 communicate with each other. By moving the sample dispensed in the dispensing region 34 to the thermal cycle region 32 such that the sample continuously reciprocates between reaction regions maintained at a predetermined temperature that are included in the thermal cycle region 32, a thermal cycle can be applied to the sample.

When the reaction processing vessel 10 is mounted on a reaction processor described later, the thermal cycle region 32 of the channel 12 includes a reaction region (hereinafter referred to as "medium temperature region 38") maintained at a relatively low temperature (about 55° C.), a reaction region (hereinafter referred to as "high temperature region 36") maintained at a higher temperature (about 95° C.), and a connection region 40 connecting the high temperature region 36 and the medium temperature region 38. The high temperature region 36 is located on the side of the first air communication port 24, and the medium temperature region 38 is located on the side of the second air communication port 26 (in other words, on the dispensing region 34 side).

The high temperature region 36 and the medium temperature region 38 each include a serpiginous shape channel where a turn is continuously made by combining curved portions and straight portions. In a case where a serpiginous shape channel is used as described above, an effective area that is limited such as that of a heater or the like constituting a temperature control means described later can be effectively used, and there are advantages that temperature variance in the reaction region is easily reduced and that the substantial size of the reaction processing vessel can be reduced, contributing to the downsizing of the reaction processor. The connection region 40 may be a linear channel.

The dispensing region 34 of the channel 12 is located between the medium temperature region 38 in the thermal cycle region 32 and the second filter 30. As described above, the dispensing region 34 has a dispensing function of extracting a predetermined amount of the sample to be subjected to PCR. The dispensing region 34 includes a dispensing channel 42 for defining a predetermined amount of the sample, two branch channels (a first branch channel 43 and a second branch channel 44) branching from the dispensing channel 42, a first sample introduction port 45 arranged at an end of the first branch channel 43, and a second sample introduction port 46 arranged at an end of the second branch channel 44. The first sample introduction port 45 communicates with the dispensing channel 42 via the first branch channel 43. The second sample introduction port 46 communicates with the dispensing channel 42 via the second branch channel 44. The dispensing channel 42 is a serpiginous shape channel in order to dispense a predetermined amount of the sample using a minimum area. The first sample introduction port 45 and the second sample introduction port 46 are formed so as to be exposed on the upper surface 14b of the substrate 14. The first sample introduction port 45 is formed to have a comparatively small diameter, and the second sample introduction port 46 is formed to have a relatively large diameter. When a branch point at which the first branch channel 43 branches from the dispensing channel 42 is defined as a first branch point 431 and a branch point at which the second branch channel 44 branches from the dispensing channel 42 is defined as a second branch point 441, the volume of the sample to be subjected to PCR is almost determined by the volume inside the dispensing channel 42 between the first branch point 431 and the second branch point 441.

In the present embodiment, the dispensing region 34 is provided between the thermal cycle region 32 and the second filter 30. However, the position of the dispensing region 34 is not limited thereto, and the dispensing region 34 may be provided between the thermal cycle region 32 and the first filter 28. As long as the dispensing can be done accurately using a pipette or the like, the channels may be formed without providing the dispensing region 34 or formed such that the sample can be introduced directly into the thermal cycle region 32 or the like.

In the reaction processing vessel 10 according to the present embodiment, the channel 12 further includes two branch channels (a first branch channel 61 and a second branch channel 62) arranged in parallel between the high temperature region 36 of the thermal cycle region 32 and the first air communication port 24. In other words, although the channel 12 is a single channel in the thermal cycle region 32, the channel 12 branches to the first branch channel 61 and the second branch channel 62 at a branching part 63 located near the high temperature region 36. The first branch channel 61 and the second branch channel 62 extend so as to pass through different parts of the substrate 14 and join again at one end 12a of the channel 12. As shown in FIG. 1A, the first branch channel 61 extends upward from the branching part 63 so as to become away from the high temperature region 36, then bends to the left with a relatively small curvature radius, and reaches one end 12a of the channel 12. On the other hand, the second branch channel 62 extends to the left from the branching part 63 so as to pass through the vicinity of the high temperature region 36, and then reaches one end 12a of the channel 12. In the present embodiment, a bent part of the second branch channel 62 is bent upward with a larger curvature radius than that of a bent part of the first branch channel 61. This allows an effect to be expected where a mass of liquid is less likely to concentrate locally. However, the form of bending is not limited to this, and a skilled person may appropriately design the bending form according to the size of the reaction processing vessel and the convenience in terms of the design and construction of the reaction processor.

The first air communication port 24, the second air communication port 26, the first filter 28, the second filter 30, the first sample introduction port 45, and the second sample introduction port 46 are exposed on the upper surface 14b of the substrate 14. Therefore, in order to seal the first air communication port 24, the second air communication port 26, the first filter 28, and the second filter 30, the first sealing film 18 is attached to the upper surface 14b of the substrate 14. In order to seal the first sample introduction port 45 and the second sample introduction port 46, the second sealing film 20 is attached to the upper surface 14b of the substrate 14. In a state where the first sealing film 18 and the second sealing film 20 are attached, the entire channel forms a closed space.

The first sealing film 18 that is used has a size that allows the first air communication port 24, the second air communication port 26, the first filter 28, and the second filter 30 to be sealed at the same time. A pressure-type pump (described later) is connected to the first air communication port 24 and the second air communication port 26 by perforating the respective parts of the first sealing film 18 that correspond to the first air communication port 24 and the second air communication port 26 by a hollow needle (syringe needle with a sharp tip) provided at the tip of the pump. Therefore, the first sealing film 18 is preferably a film made of a material that is easily perforated by the needle and/or have a thickness that is easily perforated by the needle. In the present embodiment, the sealing film having a size that is capable of sealing the first air communication port 24, the second air communication port 26, the first filter 28, and the second filter 30 at the same time is described. However, these air communication ports and filters may be sealed separately. Further, the film sealing the first air communication port 24 and the second air communication port 26 may be peeled off so as to be connected to a pressure-type pump.

As the second sealing film 20, a sealing film having a size that is capable of sealing the first sample introduction port 45 and the second sample introduction port 46 is used. Introduction of a sample into the channel 12 through the first sample introduction port 45 and the second sample introduction port 46 is performed by once peeling the second sealing film 20 from the substrate 14, and, after the introduction of a predetermined amount of sample, the second sealing film 20 is put back being attached to the upper surface 14b of the substrate 14 again. Therefore, as the second sealing film 20, a film is desired that is sticky enough to hold up through several cycles of attaching and peeling. Alternatively, as the second sealing film 20, a new film may be attached after the introduction of a sample. In this case, the importance of the property related to repetitive attaching and peeling can be lessened.

In the same way as in the channel sealing film 16, the first sealing film 18 and the second sealing film 20 may have an adhesive layer or a functional layer exhibiting stickiness or adhesiveness by pressing that is formed on one of the main surfaces thereof. In this respect, a transparent film made of a resin such as a cycloolefin polymer, polyester, polypropylene, polyethylene or acrylic is suitable but is not limited thereto. As described above, the property such as stickiness or the like desirably do not degrade to such an extent that the use is affected even after attaching and peeling of multiple times. However, in a case where a new film is attached after the peeling and the introduction of a sample or the like or after the connection to a pressure-type pump, the importance of this property related to the attaching and peeling can be lessened.

An explanation will be given next regarding a method of using the reaction processing vessel 10 formed as described above. First, a sample to be amplified through a thermal cycle is prepared. The sample includes, for example, those obtained by adding a fluorescent probe, a thermostable enzyme and four types of deoxyribonucleoside triphosphates (dATP, dCTP, dGTP, dTTP) as PCR reagents to a mixture containing one or more types of DNA. Further, a primer that specifically reacts to DNA subjected to a reaction process is mixed. Commercially available real-time PCR reagent kits and the like can be also used.

Next, the second sealing film 20 is peeled off from the substrate 14 such that the first sample introduction port 45 and the second sample introduction port 46 are open.

Figure 4:
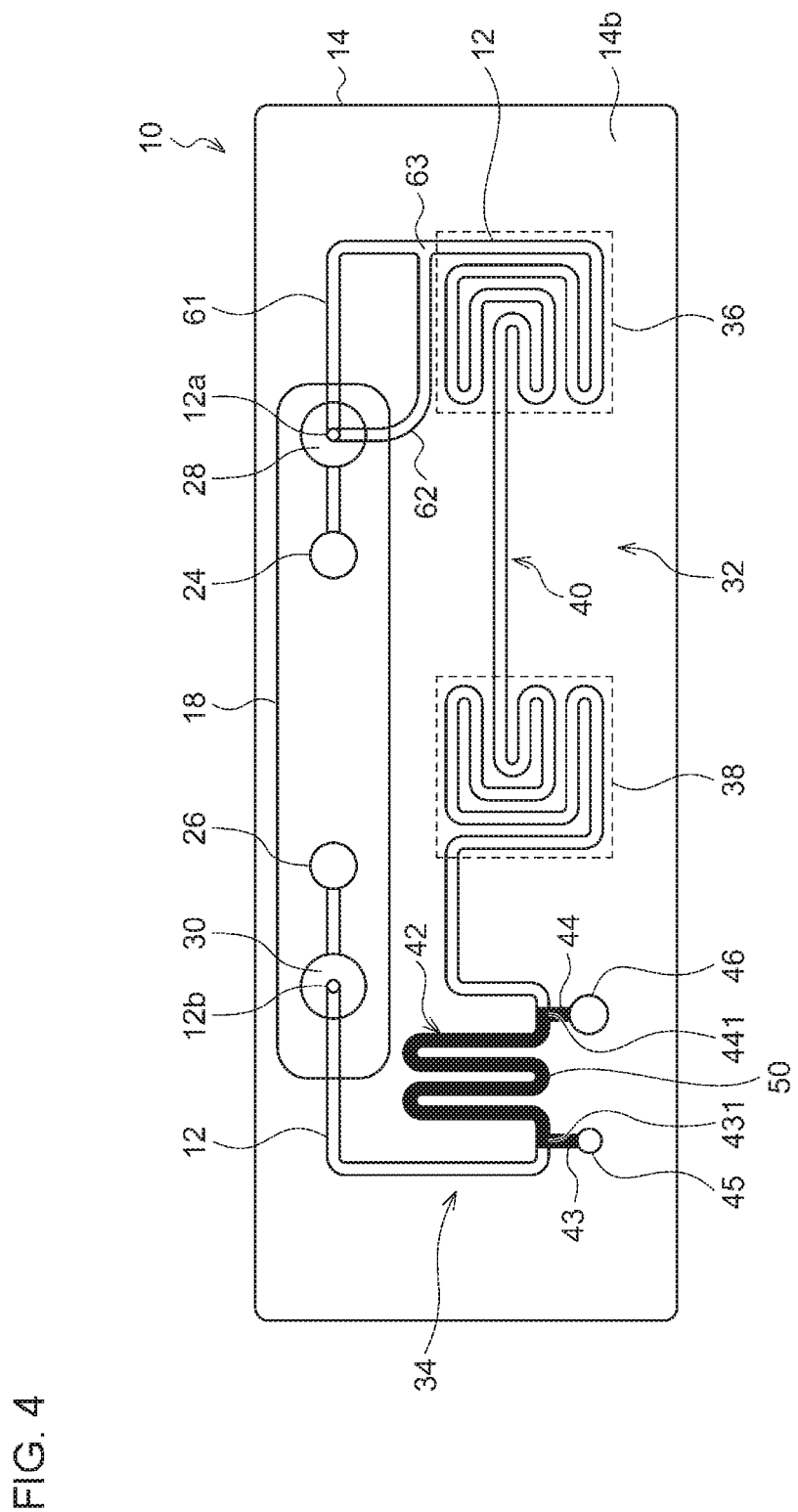
FIG. 4 is a diagram schematically showing a state where a sample is introduced into the reaction processing vessel.

The sample is then introduced to a sample introduction port by a dropper, a syringe, or the like. FIG. 4 schematically shows a state where a sample 50 is introduced into the reaction processing vessel 10. The sample 50 is introduced into the dispensing channel 42 through either one of the first sample introduction port 45 and the sample introduction port 46. The method for the introduction is not limited to this. Alternatively, for example, an appropriate amount of the sample 50 may be directly introduced using a pipette or a dropper. When the sample is introduced using a pipette, the sample 50 is introduced through the first sample introduction port 45, which has a relatively small diameter. In this case, the sample 50 is loaded into the dispensing channel 42 toward the second sample introduction port 46. When the sample 50 is introduced using a dropper, the sample 50 is introduced through the second sample introduction port 46, which has a relatively large diameter. In this case, the sample 50 is loaded into the dispensing channel 42 toward the first sample introduction port 45. The excess portion of the sample introduced through either one of the sample introduction ports that exceeds the volume of the branch channel becomes accumulated at the other one of the sample introduction ports. Therefore, in order to utilize the sample introduction port part as a kind of server, the sample introduction port part may be made to have a certain space. As will be described later, the sample 50 loaded into the dispensing channel 42 between the first branch point 431 and the second branch point 441 undergoes PCR by pressurization from the first air communication port 24 and the second air communication port 26. In this manner, the dispensing region 34 of the reaction processing vessel 10 performs a dispensing function of extracting a predetermined amount of sample.

Next, the second sealing film 20 is attached to the substrate 14 again such that the first sample introduction port 45 and the second sample introduction port 46 are sealed. Instead of the second sealing film 20 that has been peeled off, a new second sealing film 20 may be attached. This completes the introduction of the sample 50 into the reaction processing vessel 10.

The above-mentioned dispensing function in the reaction processing vessel is not to prevent introduction of the sample while precisely dispensing the sample with a pipette alone.

Figure 5:
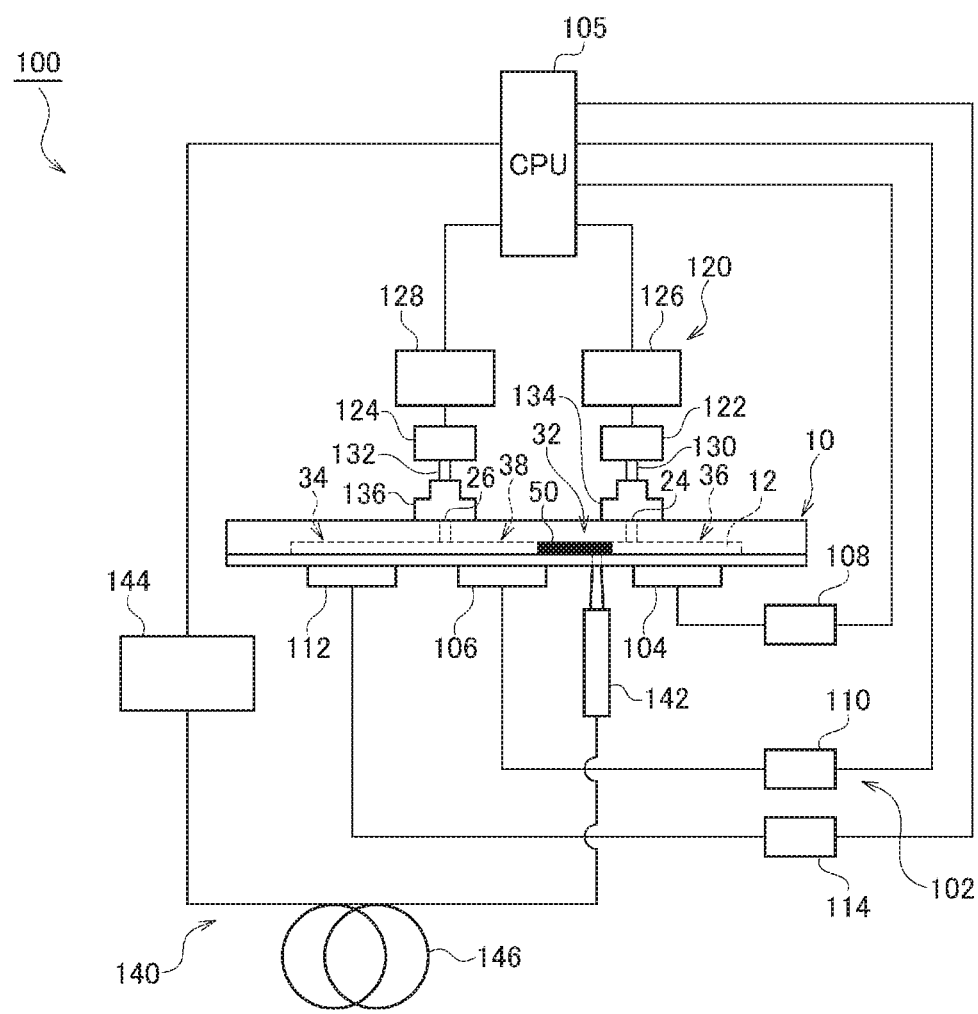
FIG. 5 is a schematic diagram for explaining a reaction processor according to an embodiment of the present invention.

FIG. 5 is a schematic diagram for explaining a reaction processor 100 according to the embodiment of the present invention.

The reaction processor 100 according to the present embodiment includes a reaction processing vessel placing portion (not shown) on which the reaction processing vessel 10 is placed, a temperature control system 102, and a CPU 105. As shown in FIG. 5, relative to the reaction processing vessel 10 placed on the reaction processing vessel placing portion, the temperature control system 102 is formed so as to be able to accurately maintain and control the temperature of the high temperature region 36 in the channel 12 of the reaction processing vessel 10 to be about 95° C. (high temperature region) and the temperature of the medium temperature region to be about 60° C.

The temperature control system 102 is for maintaining the temperature of each temperature region of a thermal cycle region and is specifically provided with a high temperature heater 104 for heating the high temperature region 36 of the channel 12, a medium temperature heater 106 for heating the medium temperature region 38 of the channel 12, a temperature sensor (not shown) such as, for example, a thermocouple or the like for measuring the actual temperature of each temperature region, a high temperature heater driver 108 for controlling the temperature of the high temperature heater 104, and a medium temperature heater driver 110 for controlling the temperature of the medium temperature heater 106. Further, the reaction processor 100 according to the present embodiment includes a dispensing heater 112 for heating the dispensing region 34 of the channel 12 and a dispensing heater driver 114 for controlling the temperature of the dispensing heater 112. Information on the actual temperature measured by the temperature sensor is sent to the CPU 105. Based on the information on the actual temperature of each temperature region, the CPU 105 controls each heater driver such that the temperature of each heater becomes a predetermined temperature. Each heater may be, for example, a resistance heating element, a Peltier element, or the like. The temperature control system 102 may be further provided with other components for improving the temperature controllability of each temperature region.

The reaction processor 100 according to the present embodiment is further provided with a liquid feeding system 120 for moving and stopping the sample 50 inside the channel 12 of the reaction processing vessel 10. The liquid feeding system 120 is provided with a first pump 122, a second pump 124, a first pump driver 126 for driving the first pump 122, a second pump driver 128 for driving the second pump 124, a first tube 130, and a second tube 132.

One end of the first tube 130 is connected to the first air communication port 24 of the reaction processing vessel 10. A packing material 134 or a seal for securing airtightness is preferably arranged at the junction of the first air communication port 24 and the end of the first tube 130. The other end of the first tube 130 is connected to the output of the first pump 122. In the same way, one end of the second tube 132 is connected to the second air communication port 26 of the reaction processing vessel 10. A packing member 136 or a seal for securing airtightness is preferably arranged at the junction of the second air communication port 26 and the end of the second tube 132. The other end of the second tube 132 is connected to the output of the second pump 124.

The first pump 122 and the second pump 124 may be, for example, micro blower pumps each comprising a diaphragm pump. As the first pump 122 and the second pump 124, for example, micro blower pumps (MZB1001 T02 model) manufactured by Murata Manufacturing Co., Ltd., or the like can be used. While this micro blower pump can increase the pressure on a secondary side to be higher than a primary side during operation, the pressure on the primary side and the pressure on the secondary side become equal at the moment when the pump is stopped or when the pump is being stopped.

The CPU 105 controls the air supply and pressurization from the first pump 122 and the second pump 124 via the first pump driver 126 and the second pump driver 128. The air blower and/or pressurization from the first pump 122 and the second pump 124 act on the sample 50 inside the channel 12 through the first air communication port 24 and the second air communication port 26 and serves as a propulsive force to move the sample 50. More specifically, by alternately operating the first pump 122 and the second pump 124, the pressure applied to either end surface of the sample 50 becomes larger than the pressure applied to the other end, and a propulsive force relating to the movement of the sample 50 can thus be obtained. By alternately operating the first pump 122 and the second pump 124, the sample 50 can be moved in a reciprocating manner in the channel so as to be repeatedly exposed to each temperature region of the channel 12 of the reaction processing vessel 10. As a result, a thermal cycle can be applied to the sample 50. More specifically, target DNA in the sample 50 is selectively amplified by repeatedly applying a step of denaturation in the high temperature region and a step of annealing and elongation in the medium temperature region. In other words, the high temperature region can be considered to be a region of temperature at which denaturation occurs, and the medium temperature region can be considered to be a region of temperature at which annealing and elongation occurs. The time for staying in each temperature region can be appropriately set by changing the time during which the sample 50 stops at a predetermined position in each temperature region.

The reaction processor 100 according to the present embodiment is further provided with a fluorescence detector 140. As described above, a predetermined fluorescent probe is added to the sample 50. Since the intensity of a fluorescence signal emitted from the sample 50 increases as the amplification of the DNA proceeds, the intensity value of the fluorescence signal can be used as an index serving as a decision-making factor for the progress of the PCR or the termination of the reaction.

As the fluorescence detector 140, an optical fiber-type fluorescence detector FLE-510 manufactured by Nippon Sheet Glass Co., Ltd., can be used, which is a very compact optical system that allows for rapid measurement and the detection of fluorescence regardless of whether the place is a lighted place or a dark place. This optical fiber-type fluorescence detector allows the wavelength characteristic of the excitation light/fluorescence to be tuned such that the wavelength characteristic is suitable for the characteristic of fluorescence emitted from the sample 50 and thus allows an optimum optical and detection system for a sample having various characteristics to be provided. Further, the optical fiber-type fluorescence detector is suitable for detecting fluorescence from a sample existing in a small or narrow region such as a channel because of the small diameter of a ray of light brought by the optical fiber-type fluorescence detector.

The optical fiber-type fluorescence detector 140 is provided with an optical head 142, a fluorescence detector driver 144, and an optical fiber 146 connecting the optical head 142 and the fluorescence detector driver 144. The fluorescence detector driver 144 includes a light source for excitation light (LED, a laser, or a light source adjusted to emit other specific wavelengths), an optical fiber-type multiplexer/demultiplexer and a photoelectric conversion device (PD, APD, or a light detector such as a photomultiplier) (neither of which is shown), and the like and is formed of a driver or the like for controlling these. The optical head 142 is formed of an optical system such as a lens and has a function of directionally irradiating the sample with excitation light and collecting fluorescence emitted from the sample. The collected fluorescence is separated from the excitation light by the optical fiber-type multiplexer/demultiplexer inside the fluorescence detector driver 144 through the optical fiber 146 and converted into an electric signal by the photoelectric conversion element.

In the reaction processor 100 according to the present embodiment, the optical head 142 is arranged such that fluorescence from the sample 50 in the channel connecting the high temperature region and the medium temperature region can be detected. Since the reaction progresses while the sample 50 is repeatedly moved in a reciprocating manner in the channel such that predetermined DNA contained in the sample 50 is amplified, by monitoring a change in the amount of detected fluorescence, the progress of the DNA amplification can be learned in real time. Further, in the reaction processor 100 according to the present embodiment, an output value from the fluorescence detector 140 is utilized for controlling the movement of the sample 50, as described later. The fluorescence detector is not limited to an optical fiber-type fluorescence detector as long as the fluorescence detector exhibits the function of detecting fluorescence from a sample.

Figure 6:
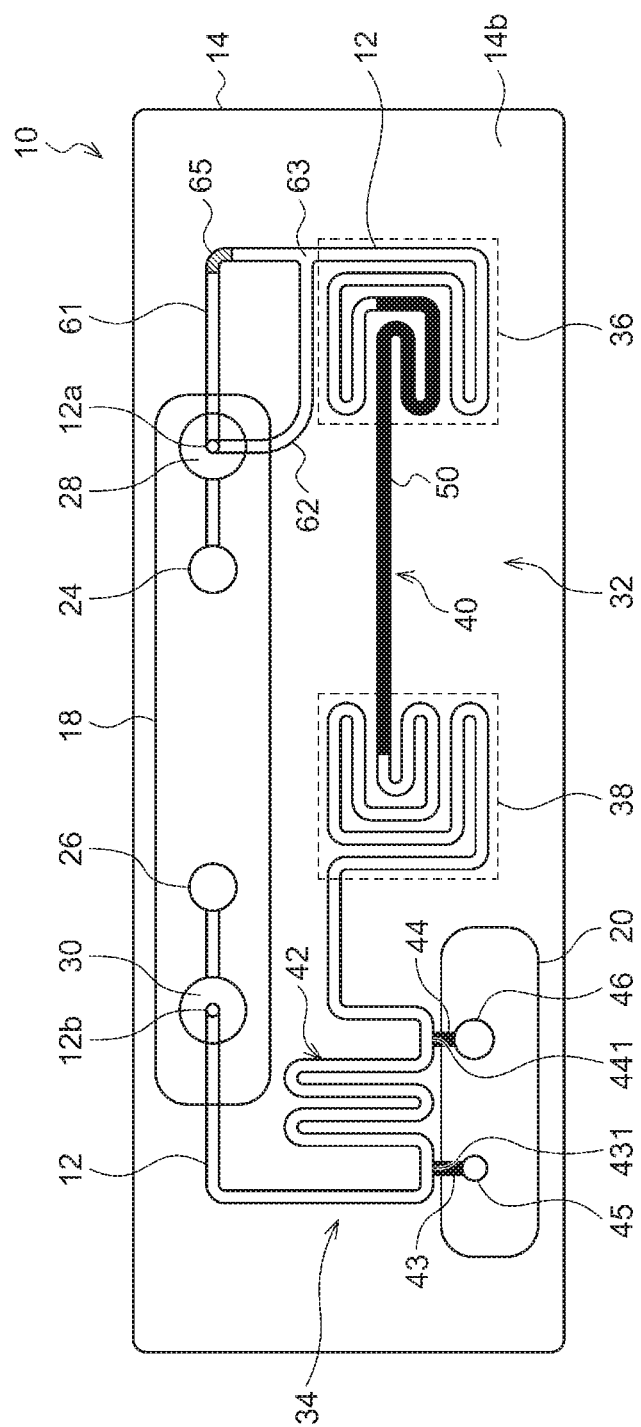
FIG. 6 is a diagram for explaining the effects of the reaction processing vessel according to the present embodiment.

FIG. 6 is a diagram for explaining the effects of the reaction processing vessel according to the present embodiment. In the reaction processing vessel 10 shown in FIG. 6, the sample 50 loaded into the dispensing channel 42 between the first branch point 431 and the second branch point 441 in the dispensing region 34 is moved to the thermal cycle region 32. More specifically, by setting the reaction processing vessel 10 filled with the sample 50 in the reaction processor 100 and operating only the second pump 124, the sample 50 in the dispensing region 34 is propelled to the thermal cycle region 32. Thereafter, as described above, by alternately operating the first pump 122 and the second pump 124 (see FIG. 5), the sample 50 is reciprocally moved in the channel 12 such that and the sample 50 is continuously moved reciprocally between the high temperature region 36 and the medium temperature region 38, and a thermal cycle can be thereby applied to the sample 50. The dispensing heater 112 may be controlled such that the temperature of the dispensing region 34, in particular, the temperatures of the first sample introduction port 45 and the second sample introduction port 46 in the dispensing region 34 when a thermal cycle is applied to the sample 50 become lower than those when the sample 50 is present in the dispensing region 34. Thereby, a situation can be prevented where the heat from the thermal cycle region 32 is transmitted to the first sample introduction port 45 and the second sample introduction port 46 and raises the temperature to push samples remaining at the first sample introduction port 45 and the second sample introduction port 46 into the channel such that the remaining samples appear inside the channel. This is because there is a possibility that the reciprocating movement of the sample 50 to be subjected to PCR may be hindered when such samples are present being spaced apart.

During the reciprocating movement between the high temperature region 36 and the medium temperature region 38 (that is, during the thermal cycle of PCR), the vapor pressure becomes high in the high temperature region 36, and the water content of the sample 50 is likely to evaporate. A portion of the water content of the sample 50 that has evaporated condenses at a part of the channel 12 where the temperature is relatively low to form a mass of liquid, which can block the channel. For example, as shown in FIG. 6, the temperature of the first branch channel 61 passing through a place distant from the high temperature region 36 tends to be low, and a liquid mass 65 tends to be generated.

However, in the reaction processing vessel 10 according to the present embodiment, even when the first branch channel 61 is blocked by the liquid mass 65 as shown in FIG. 6, the pressurization from the pump (see FIG. 5) can be applied to the sample 50 via the second branch channel 62 that is not blocked, and the sample 50 can be appropriately moved so as to perform stable PCR.

When the branching part 63 is away from the high temperature region 36, there is a possibility that a mass of liquid is generated at the branching part 63. In this case, it is difficult to apply the pressurization from the pump to the sample 50. Therefore, as shown in FIG. 6, the branching part 63 is desirably arranged near the high temperature region 36. By arranging the branching part 63 near the high temperature region 36 in this way, the heat from the high temperature region 36 is transferred to the branching part 63 such that a mass of liquid is unlikely to be generated at the branching part 63, and the pressurization from the pump can therefore be more suitably applied to the sample 50.

In the above embodiment, two branch channels are provided. However, the number of branch channels is not limited to two, and three or more branch channels may be provided between the high temperature region 36 and the first air communication port 24 in the thermal cycle region 32.

At least one branch channel out of a plurality of branch channels is desirably arranged so as to pass near the high temperature region 36. For example, in the above-described embodiment, the first branch channel 61 passes through a place distant from the high temperature region 36, and the second branch channel 62 passes near the high temperature region 36. This allows the heat from the high temperature region 36 to be transferred to the second branch channel 62 making it difficult for a mass of liquid to be generated in the second branch channel 62, and the pressurization from the pump can therefore be more suitably applied to the sample 50. In other words, this can be said as follows. If the water content of an evaporated sample forms a mass of liquid due to dew condensation or the like and the portion of the channel to be blocked is known in advance based on experience or experimentally, the blocking of such a portion can be allowed, and even in such a situation, it is possible to secure backup or bypass paths for air supply and pressurization serving as propulsive forces.

In the above embodiment, the first branch channel 61 and the second branch channel 62 each have a bent part, and the bent part of the second branch channel 62 passing near the high temperature region 36 is bent with a larger curvature radius than that of the first branch channel 61 passing through a place away from the high temperature region. In general, when the curvature radius of a bent part is large, a mass of liquid is unlikely to be generated. Therefore, by bending the bent part of the second branch channel 62 with a curvature radius larger than that of the bent part of the first branch channel 61, a mass of liquid is unlikely to be generated in the second branch channel 62, and the pressurization from the pump can therefore be more suitably applied to the sample 50. Further, in the above-described embodiment, a configuration is disclosed in which a plurality of channels are present between the high temperature region 36 and the first air communication port 24 in the thermal cycle region 32. For other channel parts, for example, a part where a portion of a channel is likely to be blocked due to a mass of liquid formed by an evaporated sample based on experience, a plurality of channels can be used.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

What is claimed is:

1. A reaction processor for causing PCR in a sample comprising:
   a reaction processing vessel comprising:
      a substrate;
      a channel for a sample to move that is provided on the substrate, the channel including a first serpiginous portion and a second serpiginous portion;
      a first air communication port and a second air communication port provided at both ends of the channel for blowing air into the channel; and
      a sample introduction port for introducing the sample into the channel provided between the first air communication port and the second air communication port;
   wherein the first air communication port, the first serpiginous portion, the second serpiginous portion and the second air communication port are provided in sequence, and
   wherein the channel includes two branch channels stemming from a portion near the first air communication port into the first serpiginous portion;
   a reaction processing vessel placing portion;
   a first heater and a second heater in contact with the reaction processing vessel, the first heater maintaining the first serpiginous portion at a first temperature to provide a first temperature region and the second heater maintaining the second serpiginous portion at a second temperature lower than the first temperature to provide a second temperature region; and
   a liquid feeding system including a micro blower pump, connecting to the first air communication port and the second air communication port, moving the sample reciprocally between the first temperature region and the second temperature region by alternately blowing air from the first air communication port and second air communication port.

2. The reaction processor according to claim 1, further comprising a fluorescence detector configured to detect fluorescence from the sample in the channel between the first serpiginous portion and the second serpiginous portion.

3. The reaction processor according to claim 1, wherein the liquid feeding system includes a first micro blower pump connecting to the first air communication port and a second micro blower pump connecting to the second air communication port,
   wherein the first micro blower pump and the second micro blower pump alternately operate and stop to blow into the channel alternately from the first air communication port and the second air communication port, to move the sample between the first serpiginous portion and the second serpiginous portion reciprocately.

4. The reaction processor according to claim 2, wherein the liquid feeding system includes a first micro blower pump connecting to the first air communication port and a second micro blower pump connecting to the second air communication port,
   wherein the first micro blower pump and the second micro blower pump alternately operate and stop to blow into the channel alternately from the first air communication port and the second air communication port, to move the sample between the first serpiginous portion and the second serpiginous portion reciprocately.

5. The reaction processor according to claim 4, wherein the first micro blower pump and the second micro blower pump alternately operate and stop based on changes in fluorescence detected by the fluorescence detector.

6. The reaction processor according to claim 1, wherein a liquid mass not subjected to PCR blocks one of the two branch channels.

7. The reaction processor according to claim 6, wherein the liquid mass comes from a condensation of a portion of an evaporated sample.

8. The reaction processor according to claim 1, further comprising;
a third serpiginous portion provided between the second air communication port and the second serpiginous portion, the third serpiginous portion having the sample introduction port for introducing the sample into the channel; and
a third heater maintaining the sample introduction port at a third temperature lower than the second temperature.

9. The reaction processor according to claim 1, further comprising;
a first filter provided between the first air communication port and the two branch channels and a second filter provided between the second air communication port and the second serpiginous region.

\* \* \* \* \*